US008663924B2

(12) United States Patent
Happe et al.

(10) Patent No.: US 8,663,924 B2
(45) Date of Patent: Mar. 4, 2014

(54) QUANTITATIVE PCR-BASED METHOD TO PREDICT THE EFFICIENCY OF TARGET ENRICHMENT FOR NEXT-GENERATION SEQUENCING USING REPETITIVE DNA ELEMENTS (LINES/SINES) AS NEGATIVE CONTROLS

(75) Inventors: Scott Happe, Austin, TX (US); Joseph Hoang Hai Ong, Austin, TX (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/308,482

(22) Filed: Nov. 30, 2011

(65) Prior Publication Data
US 2013/0137582 A1     May 30, 2013

(51) Int. Cl.
*C12Q 1/68*     (2006.01)
*C40B 30/04*     (2006.01)
*C40B 40/06*     (2006.01)
*C40B 40/08*     (2006.01)

(52) U.S. Cl.
USPC ......... 435/6.12; 435/6.1; 435/6.11; 435/91.1; 506/9; 506/16; 506/17; 506/26; 536/22.1; 536/23.1

(58) Field of Classification Search
USPC ........... 506/9, 16, 17, 26; 435/6.1, 6.11, 6.12, 435/99.1; 536/22.1, 23.1
See application file for complete search history.

(56) References Cited

U.S. PATENT DOCUMENTS

| 5,723,591 A | 3/1998 | Livak et al. |
| 2009/0318305 A1 | 12/2009 | Lin et al. |
| 2011/0184161 A1 | 7/2011 | Albert |

FOREIGN PATENT DOCUMENTS

| EP | 2053132 | 4/2009 |
| WO | WO2011009941 | 1/2011 |

OTHER PUBLICATIONS

Tawhey et al. (Genome Biology, 2009, 10:R116).*
Smit (Current Opinion in Genetics & Development, 1996, 6:743-748).*
Aird, Daniel, et al., "Analyzing and minimizing PCR amplification bias in Illumina sequencing libraries"; Genome Biology 2011, 12:R18 (http//genomebiology.com/2011/12/2/R18) (14 pages).
Buehler, Bernd, et al., "Rapid quantification of DNA libraries for next-generation sequencing"; Elsevier Inc., Methods 50 (2010); doi:10.1016/j.ymeth.2010.01.004; pp. S15-S18.
Communication and Extended European Search Report, EP Application No. 12190673, Dated Apr. 16, 2013, 7 pages.

* cited by examiner

*Primary Examiner* — Christopher M Babic
*Assistant Examiner* — Jeremy C Flinders

(57) ABSTRACT

A method for determining an efficiency of target enrichment from a DNA library, includes: adding a negative control sequence and a positive control sequence to the DNA library, or picking a negative control sequence and/or a positive control sequence from the library; determining a pre-capture amount of the negative control sequence and a pre-capture amount of the positive control sequence; performing enrichment of a target sequence from the DNA library using a bait sequence to produce a post-capture library; determining a post-capture amount of the negative control sequence and a post-capture amount of the positive control sequence in the post-capture library; and determining the efficiency of the target enrichment, based on the post-capture amount of the positive control sequence, the post-capture amount of the negative control sequence, the pre-capture amount of the positive control sequence, and the pre-capture amount of the negative control sequence.

12 Claims, 11 Drawing Sheets

FIG. 2

```
PRIMER PICKING RESULTS FOR AluJo
No mispriming library specified
No hyb oligo mishyb library specified
Using 1-based sequence positions
OLIGO          start   len    tm     gc%    any   3'    seq
LEFT PRIMER     149    20   60.69  60.00   6.00  0.00  GTGGCATGCACCTCTAGTCC
RIGHT PRIMER    282    20   59.12  55.00   5.00  2.00  TGAGACAGGGTCTTGCTCTG
HYB OLIGO       173    20   60.40  60.00   6.00  0.00  TACTCAGGAGGCTGAGGTGG
SEQUENCE SIZE: 311
INCLUDED REGION SIZE: 311
PRODUCT SIZE: 134, PAIR ANY COMPL: 5.00, PAIR 3' COMPL: 2.00
EXCLUDED REGIONS (start, len)*: 1,136

1 AGCTGGGCGTGGTGGCTCACGCCTGTAATCCCAGAACTTTGGGAGGCTGAGACTGGCTGA
     xxxxxxxxxxxxxxxxxxxxxxxxxxxxxxxxxxxxxxxxxxxxxxxxxxxxxxxxxxxx
  61 TTTCTTGAGCCCAGGAGTTTGAGACTAGCCTGGACAACATAGTGAGACCCCATCTTTACA
     xxxxxxxxxxxxxxxxxxxxxxxxxxxxxxxxxxxxxxxxxxxxxxxxxxxxxxxxxxxx
 121 AAAAATTAAAAAAAATTAGTGGACATGGTGCATGCACCTCTAGTCCCAGTTACTCAGG
                                 >>>>>>>>>>>>>>>>>>>>           ^^^^^^^
 181 AGGCTGAGGTGGGAGGATCACCTGTGCCCAGGCTGAGGCTGCAGTGAGCCATGATCACGC
     ^^^^^^^^^^^^^
 241 CACTGCACTCCAGCCTGCGTGACAGAGCAAGACCCTGTCTCAAAAGAAAAGAAAAAAAAA
                            <<<<<<<<<<<<<<<<<<<<
 301 GAAGAAAGAAA KEYS (in order of precedence):
xxxxxx excluded region
>>>>>> left primer
<<<<<< right primer
^^^^^^ hyb oligo
```

FIG. 3

```
PRIMER PICKING RESULTS FOR L1MEe
No mispriming library specified
No hyb oligo mishyb library specified
Using 1-based sequence positions
OLIGO          start  len    tm    gc%    any    3'    seq
LEFT PRIMER      70    20  60.10  40.00  4.00  2.00  GCGCAAAGCAAATAACCAAT
RIGHT PRIMER    148    20  59.32  45.00  6.00  2.00  TGTTTGCACCTCGAAGGTTA
HYB OLIGO       106    20  59.42  45.00  6.00  0.00  TGGGCTAGCAAAATCAGACA
SEQUENCE SIZE: 153
INCLUDED REGION SIZE: 153
PRODUCT SIZE: 79, PAIR ANY COMPL: 5.00, PAIR 3' COMPL: 3.00

1 ATGCTATTTACGAGAGAAGCATTTGCAACAAAATGCCAAAGAGAAGGTGAAAATAGCTGG

61 AAAAAAAAATGCGCAAAGCAAATAACCAATATAGAAAAGAAAGCCAAGTTGGGCTAGCAAAATC
                          >>>>>>>>>>>>>>>>>>>>              ^^^^^^^^^^^^^^^^

121 AGACAAAATAACCTTCGAGGTGCAAACAACTTT
    ^^^^^             <<<<<<<<<<<<<<<<<<<<

KEYS (in order of precedence):
>>>>>  left primer
<<<<<  right primer
^^^^^  hyb oligo
```

QUANTITATIVE PCR-BASED METHOD TO PREDICT THE EFFICIENCY OF TARGET ENRICHMENT FOR NEXT-GENERATION SEQUENCING USING REPETITIVE DNA ELEMENTS (LINES/SINES) AS NEGATIVE CONTROLS

BACKGROUND OF INVENTION

1. Field of the Invention

The present invention relates to the field of DNA library composition analysis, particularly to methods for analyzing changes in the relative abundance of sequences in DNA libraries.

2. Background Art

The need for more efficient techniques for sequencing genomes has led to the development of the next-generation genome sequencing techniques. While these next-generation sequencing techniques have revolutionized the way genomes are sequenced, these technologies have their weakness. For example, these techniques cannot easily target specific regions of a genome.

The ability to sequence specific regions of a genome has many applications. For example, some diseases arise from mutations of only a few nucleotides. It would be inefficient to sequence the entire human genome in order to identify these few mutations. Similarly, many complex diseases involve a single nucleotide polymorphism (SNP) or a set of SNPs associated with disease risk. Identification of such SNPs in genomes is an arduous task because it involves sequencing large regions (typically, greater than 100 kilobases) of genomic DNA from affected individuals to find a single base change or to identify all sequence variants.

To facilitate such tasks, newer approaches have been developed that involve enriching the libraries for the sequences of interest prior to analysis or sequencing. After enrichment, the subset of sequences of interest can be more efficiently sequenced. The enrichment systems typically use oligonucleotide probes containing sequences surrounding the regions of interests as baits to fish (by hybridization) DNA fragments of interest from DNA libraries. These oligonucleotide probes often include handles that can facilitate the isolation of the hybridized sequences from the libraries.

An example of such enrichment systems is the SureSelect™ system available from Agilent Technologies, Inc. (Santa Clara, Calif.). The SureSelect™ system uses a biotin-avidin based selection technique to enrich the sequences of interest. This system can significantly improve the cost and process efficiency of a sequencing workflow.

FIG. 1 shows a diagram illustrating a process of enriching DNA sequences of interest from a library, using SureSelect™. As shown in FIG. 1, a genomic library sample is prepared by cloning sequence fragments into adaptors. This library is then probed with biotinylated RNA baits (i.e., RNA oligonucleotides with biotin tags). After hybridization, sequences bound to the biotinylated baits are separated from the mixture, using streptavidin-coated magnetic beads. The beads (with the bound sequences) are washed and then the RNA sequences are digested to release the enriched target sequences as single stranded DNA sequences. The DNA sequences of interest then can be amplified using PCR to produce enriched sequences for further analysis or sequencing. This enrichment method allows one to focus on the sequences of interest with relative ease.

A similar approach is recently disclosed in U.S. Patent Application Publication No. 20110184161. According to methods disclosed in this application, a sample containing fragmented, denatured genomic nucleic acid molecules is exposed under hybridizing conditions to oligonucleotide probes immobilized on a substrate. The nucleic acid molecules of interest that hybridize to the immobilized probes are then separated from other sequences, and the bound DNA fragments are eluted from the substrate to produce enriched libraries.

With such enrichment approaches, it is desirable to be able to confirm that the target sequences are indeed enriched (and to what extent) before one spends the efforts to sequence the enriched libraries. Therefore, positive control sequences and baits are often included in the enrichment processes to permit monitoring of the enrichment. If quantitative estimate of enrichment is desired, internal standard sequences also may be included. After enrichment cycles or when estimates of enrichments are desired, aliquots from the enriched libraries may be removed and analyzed, typically with an amplification technique, such as Quantitative PCR (qPCR).

Quantitative PCR (qPCR) (or real-time PCR) can be used to amplify and simultaneously quantify targeted DNA molecules. The process involves PCR to amplify one or more specific sequences in a DNA sample. At the same time, a probe (typically, a fluorescent probe) is included in the reaction mixture to provide real-time quantification. Two commonly used fluorescent probes for quantification of real-time PCR products are: (1) non-sequence-specific fluorescent dyes (e.g., SYBR® Green) that intercalate into double-stranded DNA molecules in sequence non-specific manners, and (2) sequence-specific DNA probes (e.g., oligonucleotides labeled with fluorescent reporters) that permit detection only after hybridization with the DNA targets or after incorporation into PCR products.

Examples of fluorescent reporters may include probes that have one fluorophore quenched by another group. As the probes are incorporated into the amplified sequences, fluorophore molecules or the fluorescence quencher molecules are cleaved, allowing the fluorophores to emit light. An example of this approach is the TaqMan® assay, as described in U.S. Pat. No. 5,723,591. TaqMan® assay uses two PCR primers flanking a central probe oligonucleotide. The probe oligonucleotide contains a fluorophore and a quencher. During the polymerization step in the PCR process, polymerase cleaves the probe oligonucleotide. This cleavage causes the fluorophore and the quencher to become physically separated, which causes a change in fluorescent emission. As more PCR products are produced, the intensity of the fluorescence signal increases.

With these prior art techniques, one can monitor the enrichment of DNA libraries with more confidence. However, there remains a need for methods that can be used to monitor the enrichment processes.

SUMMARY OF INVENTION

One aspect of the invention relates to methods for determining an efficiency of target enrichment from a DNA library. A method in accordance with one embodiment of the invention includes the steps of: adding a negative control sequence and/or a positive control sequence to the DNA library, or picking a negative control sequence and/or a positive control sequence from the DNA library; determining a pre-capture amount of the negative control sequence and a pre-capture amount of the positive control sequence in the DNA library; performing enrichment of a target sequence from the DNA library using at least one bait sequence to produce a post-capture library; determining a post-capture amount of the negative control sequence and a post-capture amount of the positive control sequence in the post-capture library; and determining the efficiency of the target enrichment, based on a ratio of the post-capture amount of the positive control sequence over the post-capture amount of the negative control sequence, or based on comparing: (i) a first ratio of the pre-capture amount of the positive control sequence and the pre-capture amount of the negative control sequence, and (ii) a second ratio of the post-capture amount of the positive control sequence and the post-capture amount of the negative control sequence.

Another aspect of the invention relates to methods for determining an efficiency of target enrichment from a DNA library. A method in accordance with one embodiment of the invention includes the steps of: adding a negative control sequence to the DNA library, or picking a negative control sequence form the DNA library; determining a pre-capture amount of the negative control sequence in the DNA library; performing enrichment of a target sequence from the DNA library using at least one bait sequence to produce a post-capture library; determining a post-capture amount of the negative control sequence in the post-capture library; determining the efficiency of the target enrichment by comparing the pre-capture amount of the negative control sequence and the post-capture amount of the negative control sequence, Other aspects and advantages of the invention will be apparent from the following description and the appended claims.

BRIEF DESCRIPTION OF DRAWINGS

FIG. 2 shows the sequence of AluJo and the primers and probe for the amplification and quantification of the AluJo sequence in accordance with one embodiment of the invention.

FIG. 3 shows the sequence of L1MEe and the primers and probe for the amplification and quantification of the L1MEe sequence in accordance with one embodiment of the invention.

DETAILED DESCRIPTION

Figure 1:
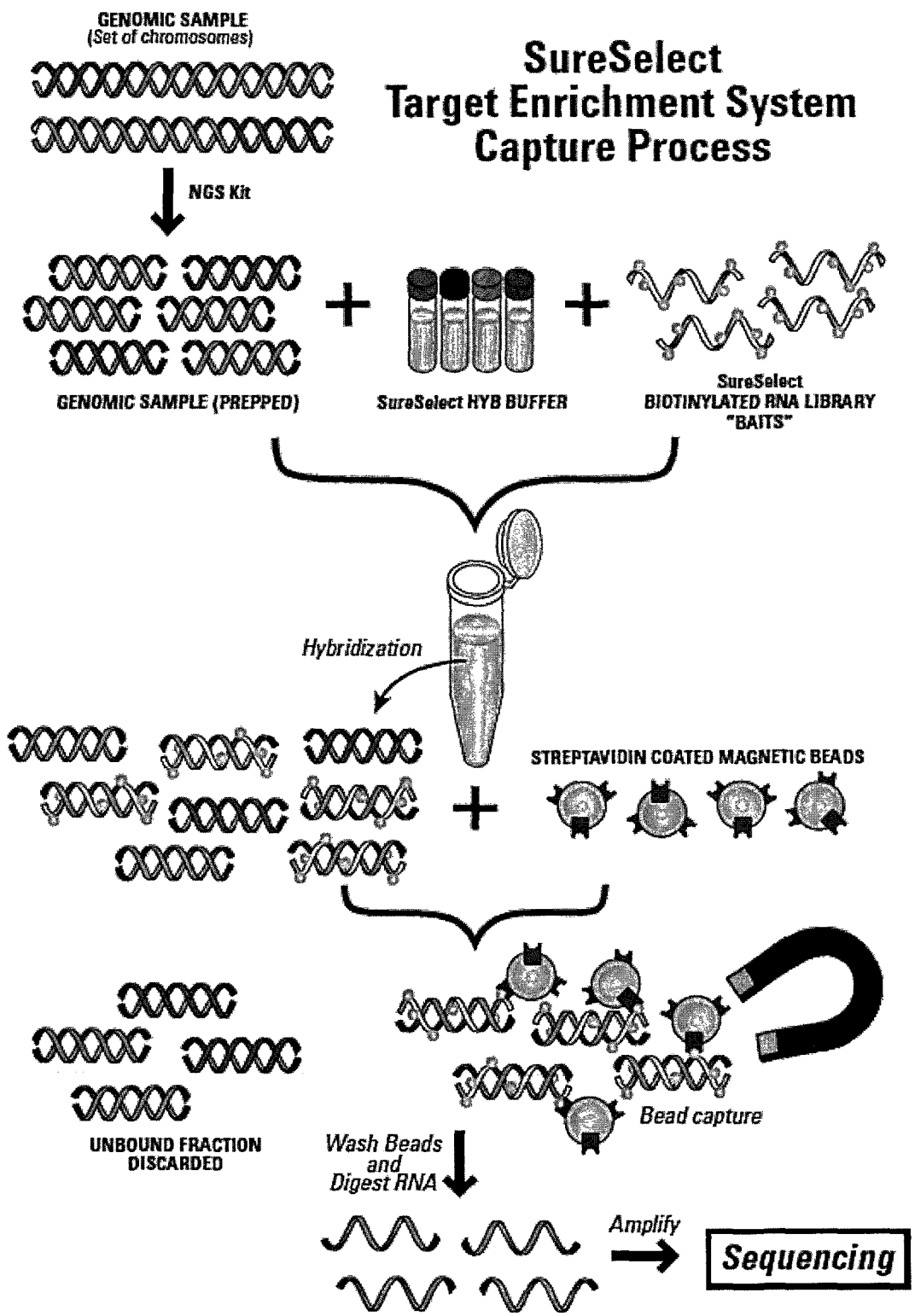
FIG. 1 shows schematic illustrating a process of target enrichment using a SureSelect™ system from Agilent Technologies.

Embodiments of the invention relate to methods for monitoring enrichment of sequences of interest from DNA libraries. As noted above, in the processes of enriching sequences of interest from DNA libraries, inclusion of positive controls has been shown to allow one to monitor the enrichment progress. Methods of the invention provide further improvements in enrichment monitoring by using negative control sequences. Methods of the invention may use negative control sequences alone or in combination with positive control sequences. Embodiments of the invention provide unexpected benefits, especially when used with positive control sequences. In addition, methods of the invention are not designed for specific libraries and, therefore have general applicability, regardless of the target libraries.

As used herein, a "negative control sequence" refers to an oligonucleotide having a selected sequence for use as a negative control in the enrichment of a target sequence form a DNA library. As described below, a negative control sequence preferably is a repeat element belonging to the SINE or LINE family.

A "positive control sequence" refers to an oligonucleotide having a selected sequence for use as a positive control in the enrichment of a target sequence form a DNA library. The positive control sequences may be those found in the DNA library or exogenous sequences that are spiked into the DNA library.

As used herein, a "bait sequence" is an oligonucleotide having a sequence selected to enrich (capture) the sequence of interest (target sequence) from a library. A bait sequence may be a DNA oligonucleotide, an RNA oligonucleotide (e.g., the baits for SureSelect™ system), or a combination of DNA/RNA oligonucleotide. A bait sequence may be linked with an affinity ligand (e.g., a biotin) to facilitate isolation of sequences bound with the bait sequence. Alternatively, the bait sequence may be attached to a solid support. Typically, in enrichment experiments, one would design one or more bait sequences around the sequence of interest (the target sequence). The bait sequences would hybridize with the target sequence. After hybridization, the bait sequences together with the bound target sequence are isolated from the mixture.

A DNA library typically comprises a large number of genomic DNA fragments. As used herein, a "DNA library" may refer to a second generation genomic library, in which the DNA fragments are flanked by specific adapters to facilitate amplification and sequencing.

"Enrichment" or "capture" refers to the process of enriching the target sequence from a DNA library using one or more bait sequences. A DNA library after enrichment of the target sequences by using one or more bait sequences will be referred to as a "post-capture library." A DNA library prior to the capture experiment may be referred to as a "pre-capture library." Accordingly, an amount (quantity) of a sequence (e.g., a positive control sequence or a negative control sequence) may be referred to as a "pre-capture amount" or a "post-capture amount," depending on whether it is prior to or after the capture experiment.

As used herein "LINE(s)" refers to "Long INterspersed Element(s)," which are a group of genetic elements that are found in large numbers in eukaryotic genomes. The 5' UTRs of LINEs typically contain promoter sequences for RNA polymerase II, while their 3' UTRs contain polyadenylation signal (AATAAA) and a poly-A tail. Therefore, LINEs may be transcribed into RNAs, using the RNA polymerase II promoters at the 5' UTRs. LINEs code for reverse transcriptases, and many LINEs also code for endonucleases (such as, RNase H). The reverse transcriptases have higher specificities for the LINE RNAs than other RNAs, and can make DNA copies of the RNAs that can be integrated into the genome at new sites. Because LINEs can copy themselves, they can enlarge the genome. The human genome, for example, contains about 500,000 LINEs, which is roughly 17% of the genome.

As used herein, "SINE(s)" refer to "Short INterspersed Element(s)," which are short DNA sequences (<500 bases) reverse-transcribed from RNA molecules, such as tRNA, rRNA, and other small nuclear RNAs. The most common SINEs in primates are Alu sequences. With about 1,500,000 copies, SINEs make up about 11% of the human genome. Among these, over one million copies are "Alu" elements, which account for about 10.7% of the human genome.

The repeat sequences in the SINEs or LINEs may be referred to as "repeat elements." "Alu sequences" or "Alu elements" refer to short stretches of DNA originally characterized by the action of the Alu restriction endonuclease. Alu sequences are generally about 300 bp long. Alu sequences are the most abundant mobile elements in the human genome and are classified as short interspersed elements (SINEs). A typical structure of an Alu element is: 5'-Part A-A5TACA6-Part B-PolyA Tail-3', wherein "Part A" and "Part B" are similar sequences, but arranged in opposite directions. The length of the polyA tail varies between Alu families. Alu sequences were split in two major subfamilies known as AluJ and AluS, and numerous sub-subfamilies. A specific example of an Alu sequence (or Alu element) is AluJo.

In accordance with embodiments of the invention, the "negative control sequences" for use to monitor the enrichment process preferably have one or more of the following properties. First, the negative control sequences should not be targets of enrichment. Therefore, the negative control sequences would be depleted in the enrichment experiments. In addition, these negative control sequences are preferably found in most libraries. If the negative controls are found in most libraries, the experimental designs with such negative control sequences would be applicable to many libraries for various enrichment purposes. Therefore, one need not redesign the negative controls when a new library is used. Finally, negative control sequences preferably are easy to monitor.

Based on these criteria, inventors of the present invention have found that repeat sequences that are often found in genomes are good negative control sequences for use with embodiments of the invention. Examples of such repeat sequences may include LINEs (long interspersed nuclear elements), SINEs (small interspersed repeat elements), and other similar sequences. These repeat sequences may be direct repeats (e.g., global direct repeat, local direct simple repeats, local direct repeats, local direct repeats with spacers, et.) or inverted repeats (e.g., global inverted repeats, local inverted repeats, inverted repeats with spacers, palindromic repeats, etc.). See e.g., Ussery et al., "Word Frequencies, Repeats, and Repeat-related Structures in Bacterial Genomes," *Computing for Comparative Microbial Genomics: Bioinformatics for Microbiologists*, Computational Biology. 8 (1st ed.), Springer, pp. 133-144 (2008). These repeat sequences may be used as negative control sequences in accordance with embodiments of the invention, whether they have biological functions or not.

Because these repeat sequences are not of interest in enrichment experiments, they are usually intentionally "masked" during target library design. Therefore, one does not have to specifically design the negative controls for each target enrichment experiment. Accordingly, using such repeat sequences for negative control monitoring can be of general utility—i.e., applicable to various DNA libraries.

As noted above, Alu repeats are extremely abundant in genomes. For example, a BLAST search for an Alu repeat yielded >91,000 hits in a human reference genome. The actual abundance of the Alu repeats is estimated to be about 1M copies/cell. Due to the large number of copies/genome, such repeats could act as sensitive measures of enrichment that may correlate with % on-target without needing to sequence the genome.

SINEs can be used as negative controls for capture, because they are automatically excluded from ELID designs by eArray™ (using the RepeatMasker algorithm). eArray™ is an online tool for designing baits for SureSelect™ captures and is available from the website of Agilent Technologies, Inc. Because SINEs are not targets for enrichment, they should be left behind (not captured) and the enriched library should show a significant reduction in the SINE sequences. In one experiment, in collaboration with Scripps Institute, it was found that that after SureSelect™ enrichment, the contents of SINEs drop from 12.6% to 4.1%. This confirms that the repeat sequences that are masked during bait design would be depleted in the enrichment (capture) experiments. More importantly, this result shows that one can use a negative control sequence alone (i.e., without using any positive controls) to get an estimate of the enrichment efficiency. That is, the extent of the depletion of the negative control sequences can be used to provide an estimate of the fold of enrichment of the target sequence.

Furthermore, in accordance with embodiments of the invention, repeat sequences that are used as negative control sequences (e.g., SINE or LINE sequences) can also be used to assess the amounts of non-specific DNA captures (i.e., % off target) because these sequences end up in the captured library by non-specific captures.

FIG. 2 shows an example of a negative control sequence, AluJo, which is a SINE and is very abundant in human genome. As shown in FIG. 2, the AluJo sequence is 311 nucleotides long (SEQ ID NO: 1). A pair of primers (left primer and right primer) and a probe oligonucleotide (20 nts each) are designed for qPCR analysis (e.g., TaqMan® assays) of this negative control sequence. The primer and probe designs for TaqMan® Assays can be performed with commercially available programs, such as the Primer Express® from Applied Biosystems (Carlsbad, Calif.) or the Primer3 from the Whitehead Institute at Massachusetts Institute of Technologies (Boston, Mass.).

The locations of the two primers and the probe oligonucleotide within the AluJo sequence are shown in FIG. 2. The sequences of these oligonucleotides are as shown below:

```
AluJo:
                                                       SEQ ID NO: 1
  1 AGCTGGGCGTGGTGGCTCACGCCTGTAATCCCAGAACTTTGGGAGGCTGAGACTGGCTGA
 61 TTTCTTGAGCCCAGGAGTTTGAGACTAGCCTGGACAACATAGTGAGACCCCATCTTTACA
121 AAAAAATTAAAAAAAATTAGTGGACATGGTGGCATGCACCTCTAGTCCCAGTTACTCAGG
181 AGGCTGAGGTGGGAGGATCACCTGTGCCCAGGCTGAGGCTGCAGTGAGCCATGATCACGC
241 CACTGCACTCCAGCCTGCGTGACAGAGCAAGACCCTGTCTCAAAAGAAAAGAAAAAAAAA
301 GAAGAAAGAAA
```

-continued

Left primer: GTGGCATGCACCTCTAGTCC

SEQ ID NO: 2

Right Primer: TGAGACAGGGTCTTGCTCTG

SEQ ID NO: 3

Probe: TACTCAGGAGGCTGAGGTGG

SEQ ID NO: 4

FIG. 2 shows one example of designing a SINE negative control sequence for use with methods of the invention FIG. 3 shows another example (i.e., L1MEe repeat), which is a LINE sequence. This L1MEe repeat (SEQ ID NO: 5) is not as abundant as AluJo in the human genome. Nevertheless, the L1MEe repeat is also a good negative control sequence. The design for a left primer (SEQ ID NO: 6), a right primer (SEQ ID NO: 7), and a probe (SEQ ID NO: 8), for using L1MEe repeat as a negative control sequence is illustrated in FIG. 3. The sequences of these oligonucleotides are as follows:

L1MEe:

SEQ ID NO: 5

```
  1 ATGCTATTTACGAGAGAAGCATTTGCAACAAAATGCCAAAGAGAAGGTGAAAATAGCTGG
 61 AAAAAAAATGCGCAAAGCAAATAACCAATAGAAAGAAAGCCAAGTTGGGCTAGCAAAATC
121 AGACAAAATAACCTTCGAGGTGCAAACAACTTT
```

SEQ ID NO: 6

Left primer: GCGCAAAGCAAATAACCAAT

SEQ ID NO: 7

Right Primer: TGTTTGCACCTCGAAGGTTA

SEQ ID NO: 8

Probe: TGGGCTAGCAAAATCAGACA

FIG. 2 and FIG. 3, respectively, show an example of a SINE sequence and a LINE sequence for use as negative control sequences and the designs of their primers and probes. One of ordinary skill in the art would appreciate that other repeat sequences (LINEs or SINEs) may be similarly designed for use as negative control sequences according to embodiments of the invention. The following are a few more repeat sequence examples that may be used as negative control sequences according to embodiments of the invention:

AluSx (Alu family, SINE repeat):

SEQ ID NO: 9

```
GGCTGGATGCAGTGGCTCGTGCCTGTAATCCCAACACTTTGGGAGGCTGA
GGCGGGTGGATCACCTGAGGTCAGGAGTTCGAGACCAGGCTGGCCAACAT
GGCAAAACCCCGCCTCTACTAAAAATACAAAAATTAGCCAGGCATAGTGG
TGCACGCCTGTAATCACAGCTACTCAAGAGGCTGAAGCAGGAGAATTGCT
TGAACTCAGGAGGTGGAGGTGGCAGTGAGCCAAGATCGTGCCACTGCACT
CCAGCCTCAGTGACAGAGCGAGACTCTGTCTCAAAAAATAAATAAATAAA
A.
```

AluY (Alu family, SINE repeat):

SEQ ID NO: 10

```
GGCCGGGCGCGGGGCTCGCGCCTGTCATCCCAGCACTTTGGGAGGCCGA
GGCGGGCGGATCACGAGGTCAGGAGATCGAGACCATCCTGGCTAACACGG
GGAAACCCCGTCTCCACTAAAAATACAAAAAGTTAGCCGGGCGCGGTGGC
GGGCGCCTGCGGTCCCAGCTGCTGGGGAGGCCGAGGCGGGAGCATGGCGG
GAACCGGGAGGCGGAGCCTGCAGTGAGCCGAGATGGCGCCACCGCACTCC
AGCCTGGGCGACCCAGCGAGACTCCGCCTCAAAAAAAAAAAAAGAA.
```

L5 (LTE family, LINE repeat):

SEQ ID NO: 11

```
TCTCTTTATTTGCTTCTGCTAATTAAAAAATCAGAGCTAAAGATACTTAA
ACACTACAGTTAAAATGCCATGGTTGTCTATTGGCTTAACGAATTCTCTT
ATGAAATCAACTCTAAAATGCTATCCATCATAAATCATGAAACGCAATTT
TTCTTATTCTCTTTAGAGCTTTACAATTCATCTTAAAGACCAGTGTTTAC
ACTCTCTTCTGTAGGTTGTACAATAACTTTTGGCGAGAAAAAATAAAAGT
CTGGCTTTCTGAC.
```

MER58A (hAT-Charlie family, DNA repeat):

SEQ ID NO: 12

```
GGAGGTGGTAAATTTGACTCATGGGACAAATCTTTTGTAAATAAAGTTTC
ACTGGAACCCAGTCACACTCATTTGTTTCTGTATTGTCTGTTGACAGTTT
```

```
TTATGCTACAATAAGAGTTGAGTAGTTATGACAGACACTCTAGGGCCTGT
AGAGCCTATAATATTTACTTTTGGCCTTTTACGGAAGAAGTTTACTGACC.
```

MLT1A (ERVL-MaLR family, LTR repeat):

SEQ ID NO: 13

```
CTCCTCTGTCTTTTCCCACCAAGTGAGGATGCGAAGAGAAGGTGGCTGTC
TGCAAACCAGGAAGAGAGCCCTCACCGGGAACCCGTCCAGCTGCCACCTT
GAACTTGGACTTCCAAGCCTCCAGAACTGTGAGGGATAAATGTATGATTT
TAAAGTCGCCCAGTGTGTGGTATTTTGTT.
```

According to embodiments of the invention, depletion of the negative control sequences after an enrichment (capture) experiment would indicate that the target sequences are enriched. Techniques for monitoring depletion of negative control sequences in the enrichment experiments may be the same as those used to monitor the enrichments of the target sequences or the positive control sequences. Typically, the monitoring techniques involve amplification of the samples, followed by quantification of the amplified samples. Alternatively, the amplification and quantification may be performed simultaneously. One such technique for simultaneous amplification and quantification is quantitative PCR (qPCR), which is also known as real-time PCR.

qPCR process involves amplification of one or more specific sequences in a DNA sample using regular PCR techniques. The PCR products are quantified in real time using a probe (typically a fluorescent probe) that is included in the reaction mixture. The fluorescence probe would give off signals based on the amount of the double-stranded DNA products to provide real-time quantification.

As noted above, two types of fluorescent probes are commonly used in the quantification of qPCR products. The first type is non-specific fluorescent dyes that intercalate into double-stranded DNA molecules in a sequence non-specific manner. Examples of such fluorescence dyes include SYBR® Green, ethidium bromide, DAPI (49,6-diamidino-2-phenylindole), Hoechst 33342, SYTO®-13 (a bis-benzimide fluorescent dye), YOYO®-1, and TOTO®-1 (a dimmer of thiazole orange). SYTO®-13, YOYO®-1, and TOTO®-1 are available from Life Technologies (Carlsbad, Calif.). These fluorescence probes typically give off little or no fluorescence signals by themselves. However, when they intercalate into double-stranded DNA or RNA molecules, the base stacking provides hydrophobic environment that allows these probes to have enhanced fluorescence. Because these dyes intercalate into double-stranded DNA or RNA molecules in a sequence non-specific manner, the intensities of the fluorescence signals would simply reflect the amounts of these dyes intercalating into the double stranded molecules. Therefore, the intensities of the fluorescence signals detected in real-time PCR in the presence of such fluorescence dyes would reflect the amounts of the double stranded products.

The second type of fluorescence probes used in qPCR for estimation of amounts of DNA products are sequence-specific DNA probes. These sequence-specific DNA probes are typically oligonucleotides labeled with fluorescent reporters (fluorophores). In addition, these sequence-specific DNA probes each would include a fluorescence quencher that suppresses the fluorescence signals from the fluorescence reporters. Only when the quencher molecules are severed from the fluorescence reporters would the signals from the fluorescence reporters become substantially increased. Because these sequence-specific probes can be used to quantify the amount of a target sequence in a mixture, it is particularly useful for estimating the amounts of specific sequences, without interference from other sequences also present in the mixture. This approach is used in the TaqMan® assays available from Applied Biosystems, Inc. (Carlsbad, Calif.). The TaqMan® assays are described in U.S. Pat. No. 5,723,591.

The use of qPCR for the rapid quantification of DNA libraries has been demonstrated recently. (Buehler et al., "*Rapid Quantification of DNA Libraries for Next-Generation Sequencing,*" Methods, 50 (2010), S15-S18). As shown in this publication, qPCR can provide accurate quantitative measurements of DNA libraries. In addition, because only those fragments containing the next-generation library adapters are amplified, qPCR can minimize overestimation of the DNA concentrations in such libraries—i.e., fragments with no or one adapters will not be amplified.

The utility of qPCR in monitoring sequence compositions in DNA libraries was recently demonstrated by Daniel Aird et al., "*Analyzing and Minimizing PCR Amplification Bias in Illumina Sequencing Libraries,*" Genome Biology, 2011, 12-R18. In this paper, the authors used qPCR to investigate biases occurring in the amplification of DNA libraries. Various factors (including GC contents) can influence the efficiencies of PCR reactions, and different PCR machines and protocols may also result in sequence biases in the amplified libraries. To assess biases, the authors used qPCR to quantify various sequences before and after amplifications to see whether different sequences are enriched to different extents. Using this monitoring technique, the authors were able to design PCR protocols that minimize the biases during PCR amplification. This study validates the utility of qPCR in sequence composition analysis of DNA libraries.

In accordance with embodiments of the invention, qPCR may be performed using commercially available instruments and the standard protocols provided by the vendor. An example of commercially available qPCR instrument is the Agilent (Strategene) Mx3005P QPCR System. This system may use Brilliant II SYBR® Green QPCR Master Mix or Brilliant III Ultra-Fast SYBR® Green Master Mix. Cycling conditions for using Brilliant II, for example, may be as follows: 10 min activation at 95° C., 40 cycles at 30 s 95° C., 60 s 60° C., and a melt curve from 70 to 95° C. Cycling conditions for Brilliant III Ultra-Fast, for example, may be as follows: 3 min activation at 95/98° C., 40 cycles at 10 s 95/98° C., 20 s 60° C., 20 s at 72° C., and a melt curve from 72 to 98° C.

The SYBR® Green based assays are non-specific and can be used to quantify all double-stranded DNA or RNA molecules. If quantifications of specific sequences are needed, the TaqMan® assays may be used. The TaqMan® assays use two primers to amplify the sequences and use specific probes for the target sequence to generate fluorescence signals. Each probe includes a fluorophore and a fluorescence quencher. The fluorescence quencher prevents the fluorophore from emitting signals. When the probe binds to the target sequence template, the exonuclease activity of the polymerase cleaves a moiety off the probe, separating the fluorophore from the fluorescence quencher. As a result, fluorescence signals from the fluorophores become detectable. One skilled in the art would appreciate that either the non-specific qPCR assays (e.g., SYBR® Green based methods) or the sequence-specific qPCR assays (e.g., the TaqMan® assays) may be used with embodiments of the invention, depending on the purpose. Furthermore, other similar qPCR quantification methods may also be used without departing from the scope of the invention.

For example, mechanism-based qPCR quantification methods may also be used. The mechanism-based qPCR methods do not require a standard curve for quantification. Mechanism-based qPCR methods, such as the two-parameter mass action kinetic model of PCR (MAK2), have been shown to have equal or better quantitative performance to standard curve methods. These mechanism-based methods use knowledge about the polymerase amplification process to generate estimates of the original sample concentration. See, Boggy G. J., Woolf P. J. (2010), "*A Mechanistic Model of PCR for Accurate Quantification of Quantitative PCR Data,*" PLoS ONE 5(8): e12355. doi:10.1371/journal.pone.0012355.

While quantification of DNA or RNA molecules are shown with qPCR in the examples described here, one skilled in the art would appreciate that other techniques for the quantification of these molecules may also be used without departing from the scope of the invention. For example, Agilent 2100 Bioanalyzer® is a useful alternative.

Quantification of the enriched libraries using a High Sensitivity DNA kit on the Agilent 2100 Bioanalyzer™ may be performed according to the manufacturer's instructions. ("Agilent High Sensitivity DNA kit Guide," available from the website of Agilent Technologies, Inc., Santa Clara, Calif.). As an example, a test sample may be diluted 1:50 and 1:100 and 1 µl was run on a primed chip along with DNA markers for size determination and quantification. The concentration may be determined on fragment sizes from 160 to 400 bp using the Bioanalyzer™ software. The data may be corrected for dilution and averaged.

Using qPCR techniques to quantify DNA concentrations standard curves are required. To construct the standard curves, typically a series of amplifications are performed using sequences of known concentrations. The number of PCR cycles needed for the amplified products to become detectable (e.g., over a threshold level) are referred to as the threshold cycles (Ct), which are inversely proportional to the initial concentrations of the sequences. Therefore, a plot of the threshold cycles (Ct) versus the logarithm of the initial concentrations would show a linear relationship.

Figure 4:
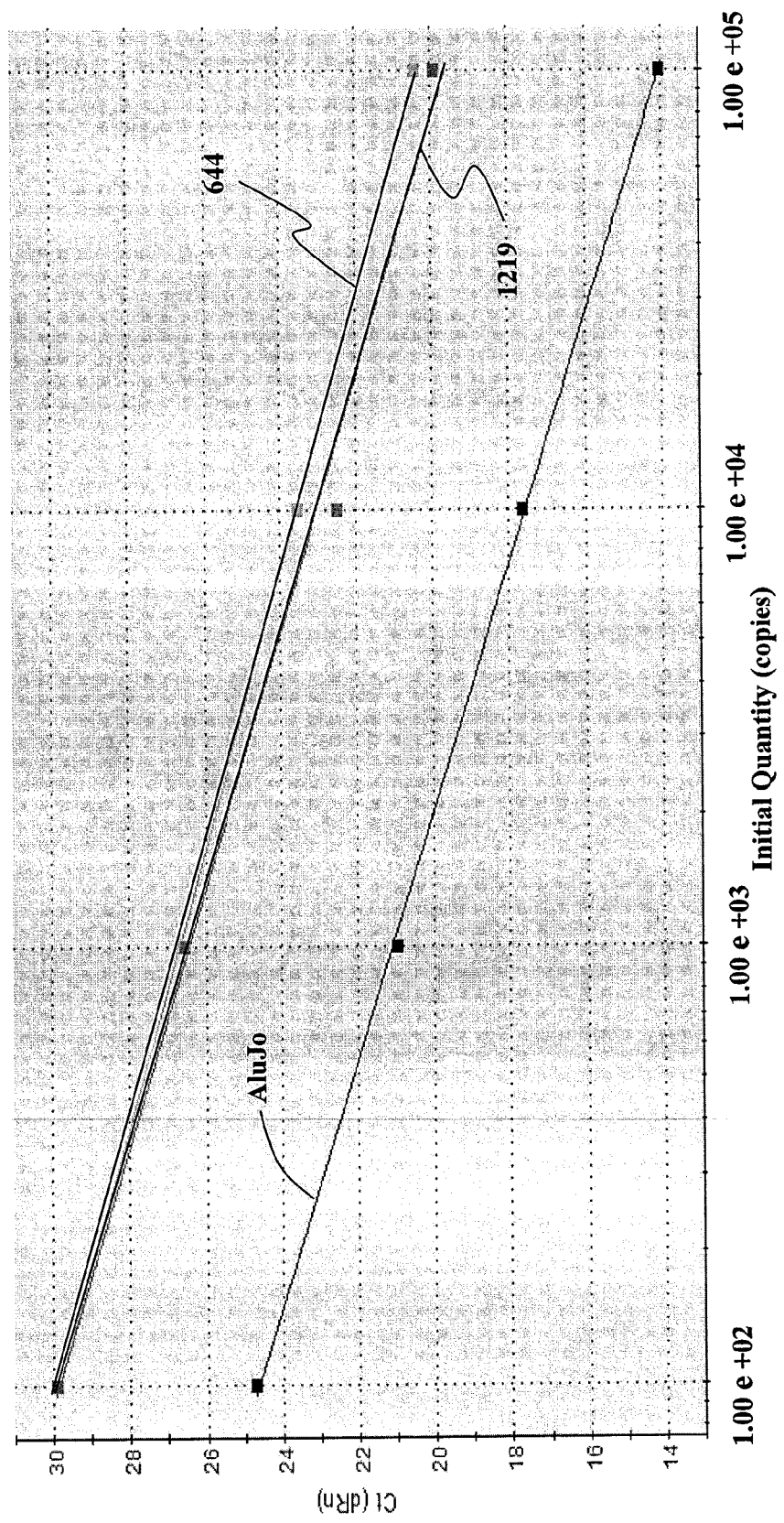
FIG. 4 shows a chart of standard curves for qPCR assays in accordance with one embodiment of the invention.

FIG. 4 shows an example of standard curves for three test sequences, 644, 1219, and AluJo. In the example shown in FIG. 4, all three sequences show good linear correlations between the initial copy numbers (from $10^2$ to $10^5$ copies) and the threshold cycles (Ct). Having such standard curves, one would be able to estimate the initial copy number for a particular sequence, if one has the threshold cycle number (Ct).

FIG. 4 also shows that the AluJo sequence is more sensitive to the qPCR quantification and can be detected at about 5 cycles earlier than the other two test sequences (644 and 1219), suggesting that the detection sensitivity of AluJo is about 32 times better than the other two sequences. The better sensitivity of AluJo sequence may result from the unique sequence contents of the repeat sequence and/or better primer/probe design. Better detection sensitivities of negative control sequences are desirable for use with embodiments of the invention.

Figure 5:
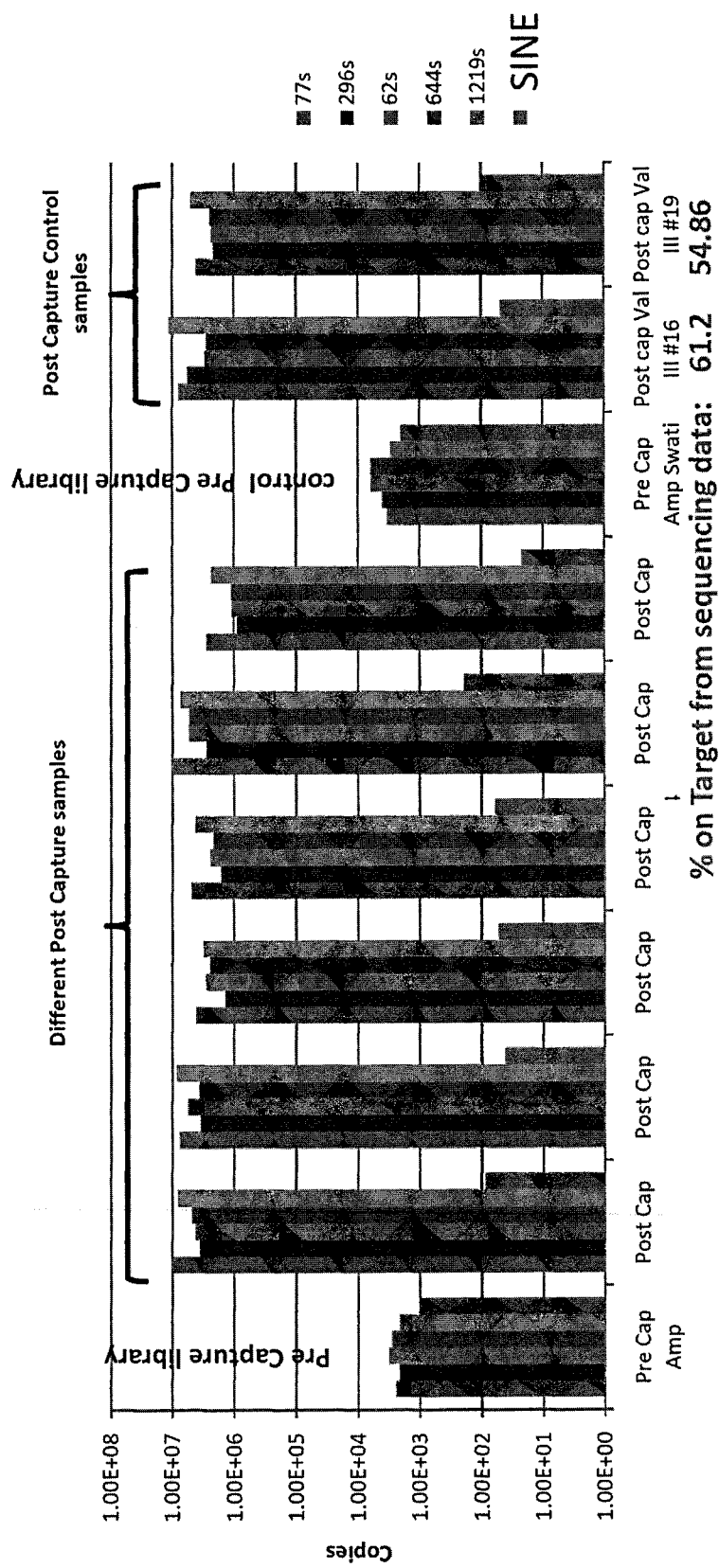
FIG. 5 shows the amounts of various positive control sequences and the SINE negative control sequence before and after a capture experiment in accordance with one embodiment of the invention.

To illustrate the utility of embodiments of the invention, a SINE sequence has been used as a negative control sequence in a series of enrichment experiments. FIG. 5 shows results of such experiments. Before the enrichment (capture) processes, the copies numbers of the SINE and five positive control sequences (77, 296, 62, 644, and 1219) are adjusted to be about the same based on the standard curve—i.e., between $1 \times 10^3$ and $1 \times 10^4$ copies each.

As shown in FIG. 5, after captures, the copy numbers of the positive control sequences all increase to about $1 \times 10^6$ and $1 \times 10^7$ copies each, while the negative control sequence (SINE) is reduced to about $1 \times 10^1$ and $1 \times 10^2$ copies. That is, all positive control sequences are enriched by bout $10^3$ folds, while the negative control sequence is reduced by a factor of about $10^2$. Thus, there are about $10^4$-$10^5$ folds more positive control sequences, as compared with the SINE negative control sequence, after the capture. These results clearly show that the enrichments of the positive control sequences work well and that the negative control sequence is indeed depleted. Sequence analyses also reveal that the on-target percentages (i.e., percentages of the target sequences in the post-capture library) are in the range of about 55%-60%.

Figure 6A:
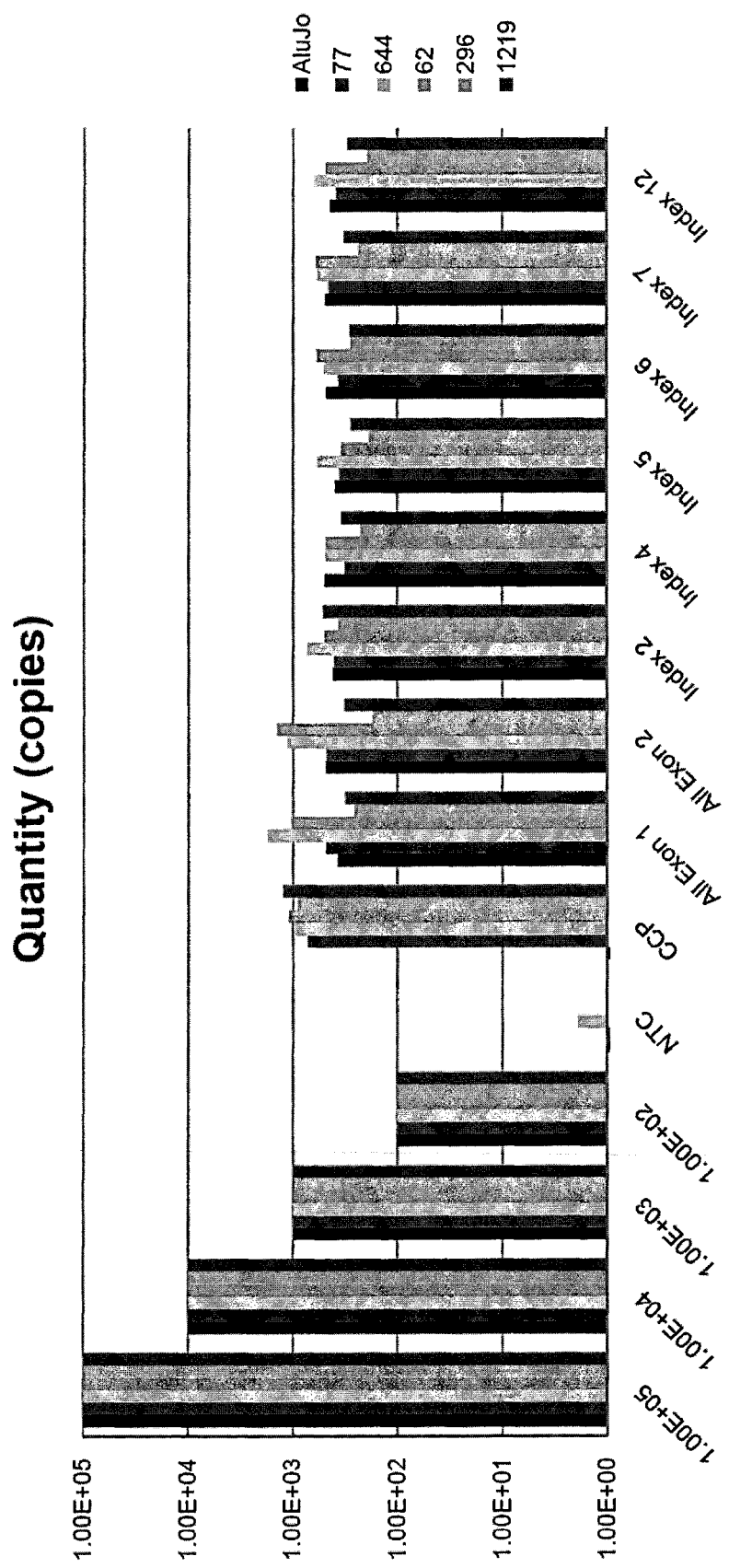
FIG. 6A shows amounts of 5 positive control sequences and one negative control sequence (AluJo) before capture experiments using various libraries.
Figure 6B:
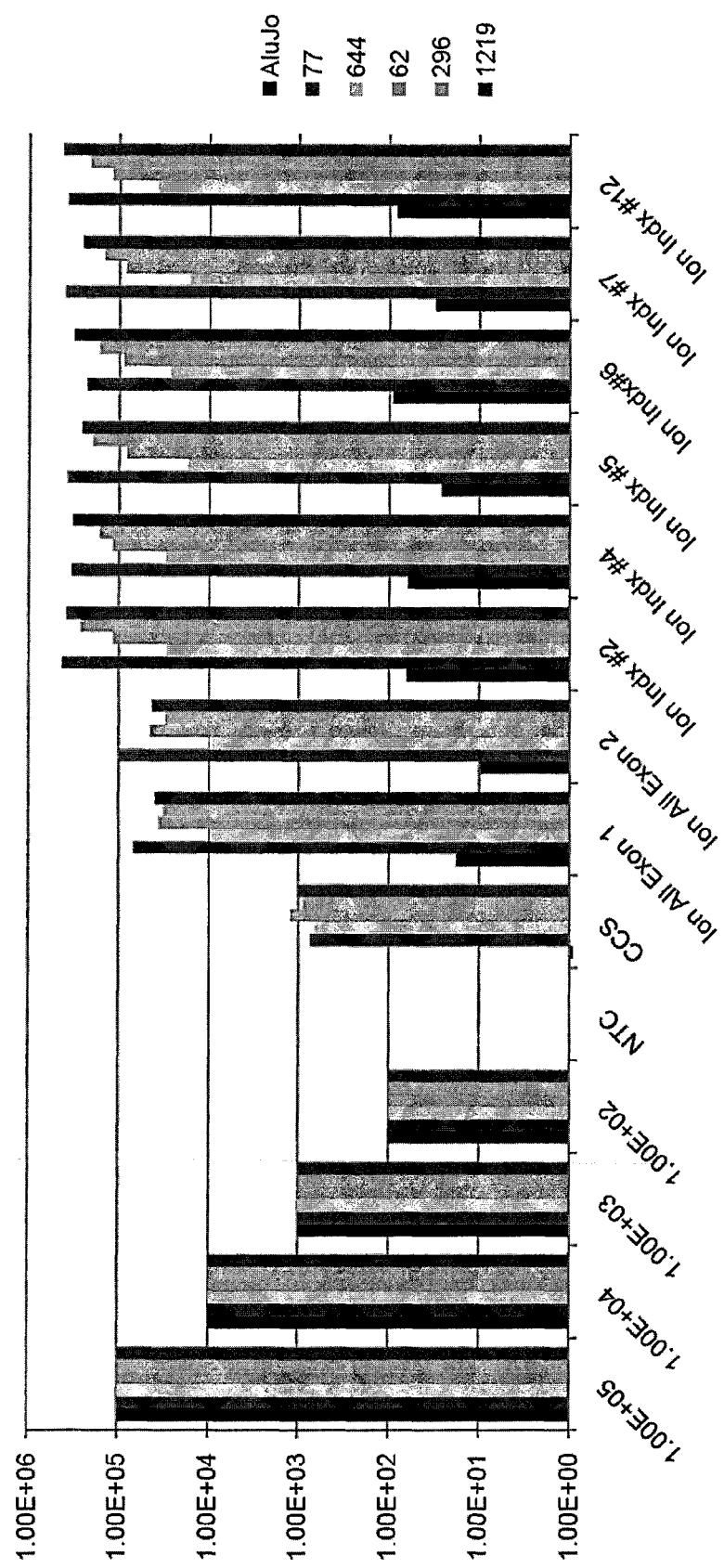
FIG. 6B shows the amounts of these sequences after the capture experiment in accordance with one embodiment of the invention.

As noted above, qPCR can also be used to quantify the sequences of interest. If quantification is desired and variations between different libraries and/or machines are of concern, one can include internal standards in the assays. For example, FIG. 6A and FIG. 6B show results from an experiment, in which an AluJo sequence is used as a negative control sequence to monitor the enrichments of five positive control sequences (i.e., 77, 644, 62, 296, and 1219) from various libraries. FIG. 6A shows the relative quantities of the various sequences in the libraries before the enrichment. In the pre-capture libraries, the positive control and negative control sequences are present at about the same amounts (about $1 \times 10^2$-$1 \times 10^3$).

FIG. 6B shows the results of the relative quantities in the libraries after the enrichment. In the post-capture libraries, the contents of the positive control sequences increase to about $1 \times 10^3$, while the contents of the negative control sequence are reduced to about $1 \times 10^1$-$1 \times 10^2$. A comparison between the pre-capture and post-capture abundances clearly indicates that the positive control sequences are significantly enriched. The enrichment is especially apparent, if one uses the ratios of the positive control sequences to the negative control sequence as yardsticks.

The experiments shown in FIG. 6A and FIG. 6B also show that a single AluJo negative control sequence can be used with a variety of libraries, illustrating the broad applicability of the method. In other words, there is no need to redesign negative control sequences when a new library is used.

To explore the various conditions for monitoring the capture processes according to embodiments of the invention, a series of experiments using five SureSelect™ baits (62, 77, 296, 644, and 1219) as positive control sequences and the AluJo sequence as a negative control sequence are performed under different conditions, e.g., different hybridization conditions, wash conditions, and/or elute conditions. These conditions are shown in the following Table:

| Sample # | Condition |
|---|---|
| Cap #1 | Old 0.2 Mb bait—Control |
| Cap #5 | New bait |
| Cap #10 | 4X Blocking Agent |
| Cap #13 | 50 X bait |
| Cap #17 | 200 X bait |
| Cap #21 | Blocker A |
| Cap #25 | Blocker B |
| Cap #29 | 2X block2 + 4X Blocking Agent |
| Cap #33 | SOLiD ® shear |
| Cap #57 | 6 cycles Pre-capture PCR |
| Cap #61 | Additional washes with 0.5X WB2 |
| Cap #65 | 70° C. wash |
| Cap #69 | Elute at 37° C. |
| Cap #37 | 70° C. Hybridization |
| Cap #41 | 48 hr Hybridization |
| Cap #45 | 4 hr Hybridization |
| Cap #49 | 2 hr Hybridization |
| Cap #53 | 2 WB1 washes |

Figure 7A:
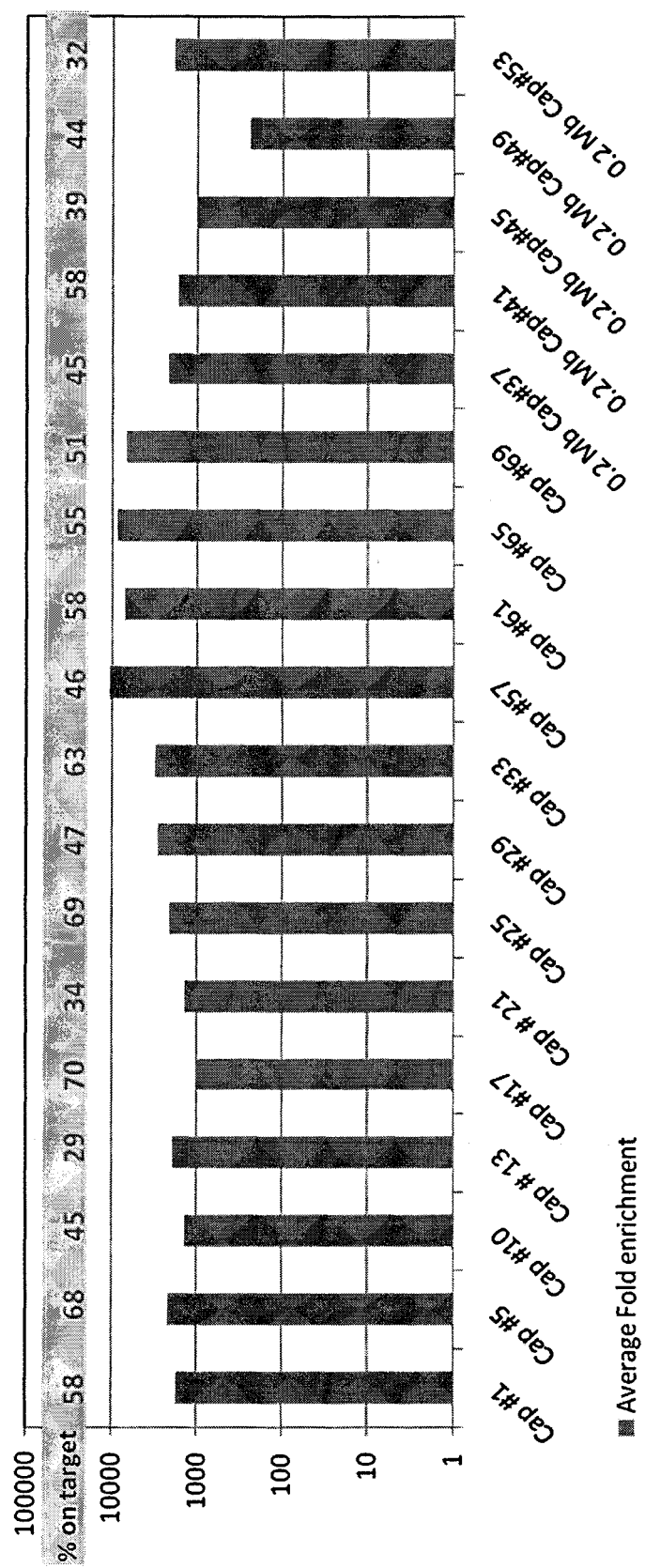
FIG. 7A shows amounts of 5 positive control sequences and one negative control sequence (AluJo) before capture experiments under various conditions.

FIG. 7A shows the fold enrichment data for the various capture experiments. The data shown are average values for all 5 positive control targets. The percentages on-target of various sequences are also shown. The % on target, which is the amount (in %) of the target sequences in the captured pool, would vary with the particular bait designs, the amounts of baits used, the capture conditions (e.g., temperatures and durations for the hybridization), wash conditions (e.g., wash buffers, temperatures, and how many times), and elution conditions (e.g., elution buffers and temperatures).

A comparison between Cap #13 (50× bait) and Cap #17 (200× bait) reveals that more baits would not increase the folds of enrichment; however, more baits significantly improve the % on target. A comparison among Cap #41 (48 hrs), Cap #45 (4 hrs), and Cap #49 (2 hrs) reveal that a longer hybridization time improves both the fold enrichment and the % on target, suggesting that annealing is a slow process.

Figure 7B:
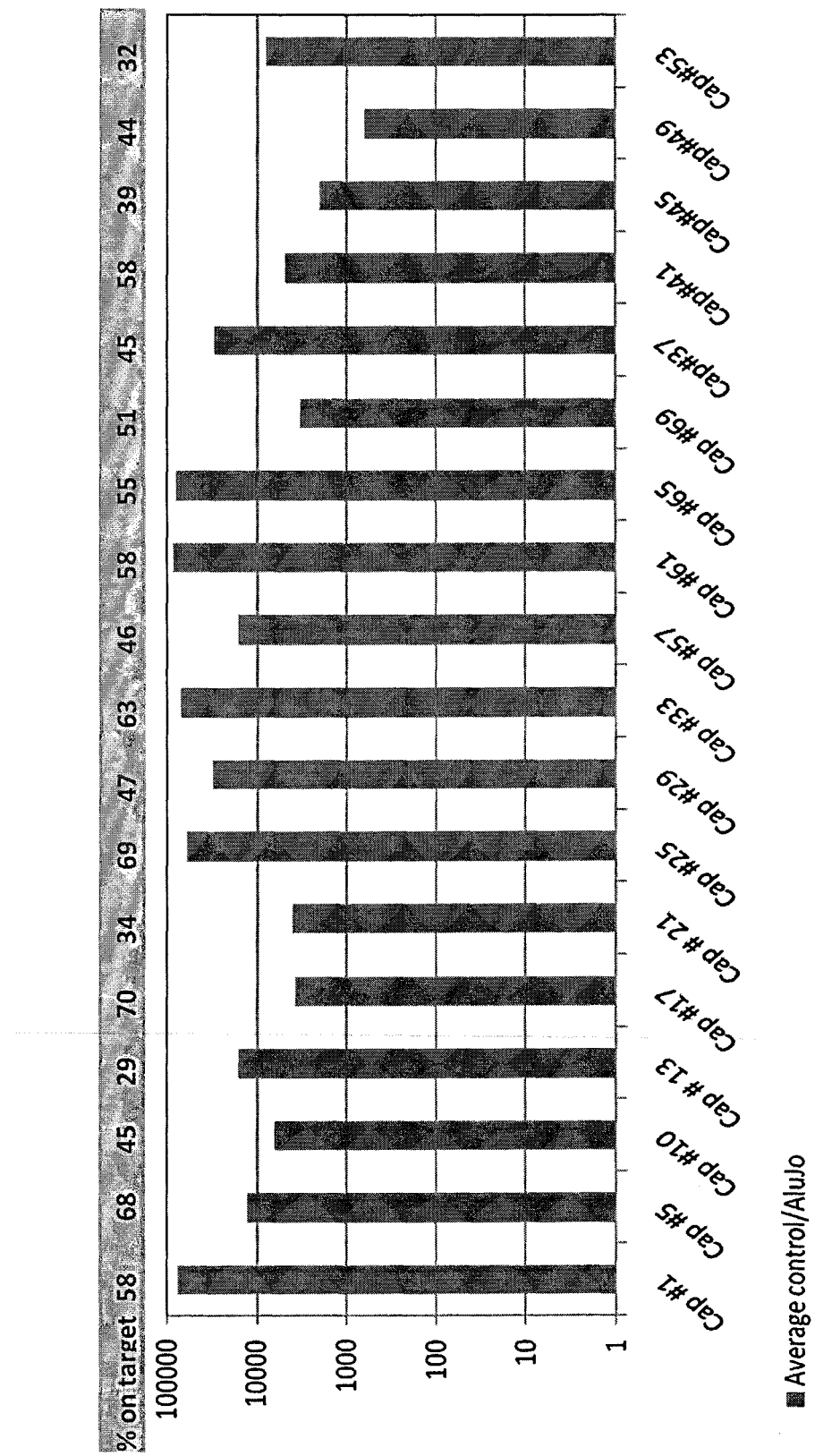
FIG. 7B shows the amounts of these sequences after the capture experiment in accordance with one embodiment of the invention.

FIG. 7B shows the fold enrichment data based on ratios of the average values of 5 control targets relative to the negative control (AluJo) sequence. It is clear that the folds of enrichment would be larger when one looks at the positive/negative ratios. For example, in FIG. 7A, the folds of enrichments for the positive sequences range from about $10^2$ to about $10^3$, while the folds of enrichment in FIG. 7B are from about $10^3$ to about $10^5$. Thus, the ratios would provide more sensitive measures of the enrichment.

Figure 8:
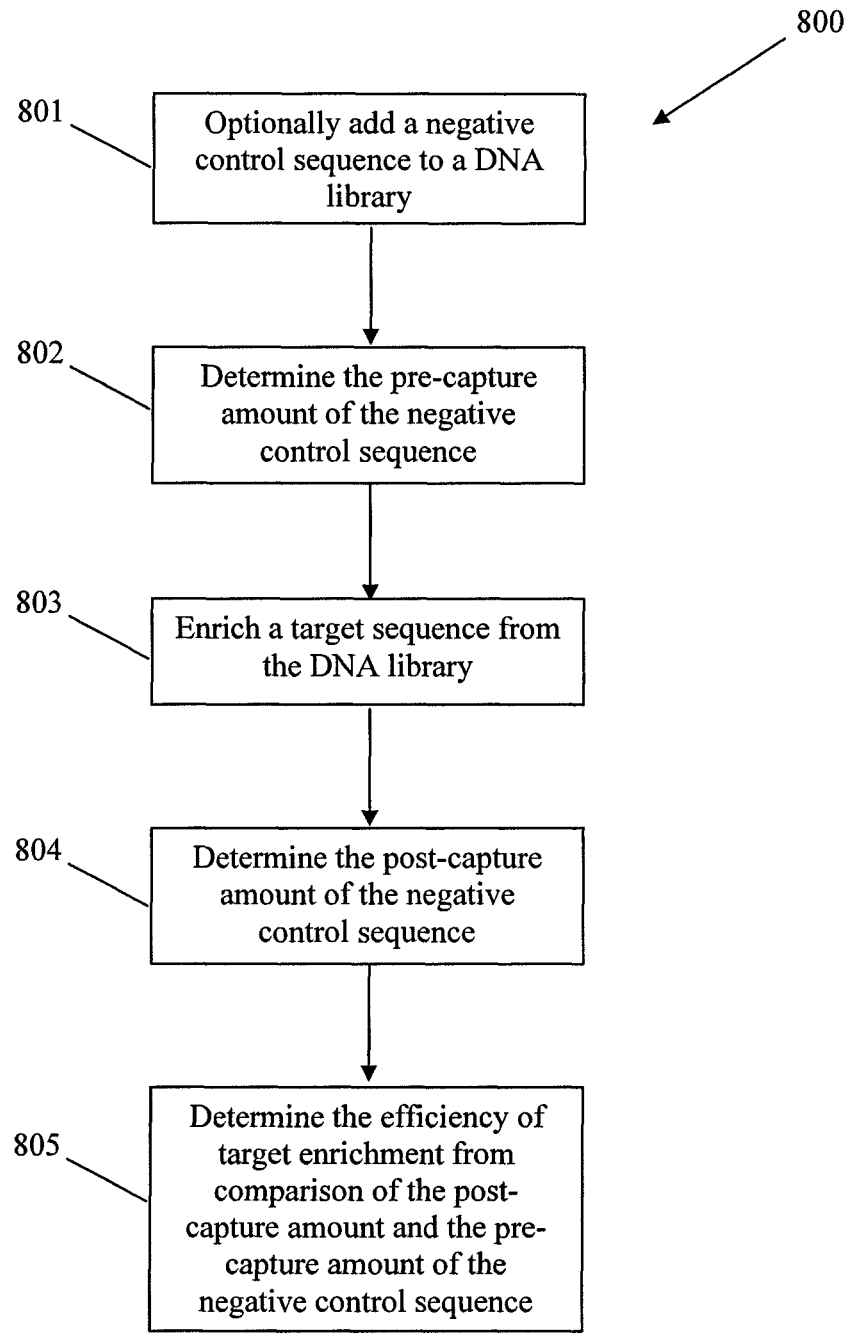
FIG. 8 shows a flowchart illustrating a method in accordance with one embodiment of the invention.

FIG. 8 shows a flow chart illustrating a method 800 in accordance with one embodiment of the invention. According to this method, one may optionally add a negative control sequence to a library, from which one or more target sequences are to be enriched. (step 801). However, in most cases, one can use one or more repeat sequences already in the library (i.e., endogenous sequences) as negative control sequences. Therefore, step 801 is unnecessary for most cases. However, if one already has a negative control sequence and its primers and probe on hand, it might be more convenient or advantageous (e.g., one can control the concentrations) to use such an exogenous negative control sequence. As described above, a negative sequence for use with embodiments of the invention preferably are selected from the repeat elements in the SINEs or LINEs family. If the amount of the negative control sequence, whether endogenous or spiked-in, in the DNA library is not known, then determine the pre-capture amount of the negative control sequence in the pre-capture library. (step 802). Determination of this amount may be performed with qPCR as described above, or with any other suitable method. If the amount of the negative control sequence added to the pre-capture library is known, then one can skip step 802. In this case, the "determining" the amounts of the negative control sequence is intended to mean "obtaining" such information.

Next, one would perform the capture or enrichment of the target sequence(s). (step 803). The capture or enrichment may be performed using any of the commercially available system and following the manufacturer's procedures. For example, the SureSelect™ system from Agilent Technologies in combination with the Illumina instrument from Illumina, Inc.

After capture, the amount of the negative control sequence in the post-capture library is determined. (step 804). Again, determination of this amount may use qPCR or any other suitable method.

Finally, the capture (enrichment) efficiency can be determined from the pre-capture amount and the post-capture amount of the negative control sequence. (step 805). The efficiency may be estimated or determined based on the extent of depletion of the negative control sequence.

For example, in the collaborative experiment with Scripps Institute described above, it was found that that the contents of SINEs drop from 12.6% to 4.1%. These numbers may be used to provide a rough indication of efficiency of the enrichment for this particular experiment. The number estimated from the pre-capture amount and the post-capture amount (i.e., about 3 fold ($12.6/4.1 \approx 3.1$)) of negative control sequences alone would most likely under estimate the actual efficiency of the enrichment. For example, based on a comparison of the negative control sequence in FIG. 6A and FIG. 6B, one would get an indication of $1 \times 10^1$-$1 \times 10^2$ fold reduction of the negative control sequence. However, the positive control sequences show $1 \times 10^2$-$1 \times 10^3$ fold enrichment. Even though this method may not provide an accurate quantitative estimate of the fold of enrichment, this estimate at least would provide an indication as to whether the enrichment worked.

Figure 9:
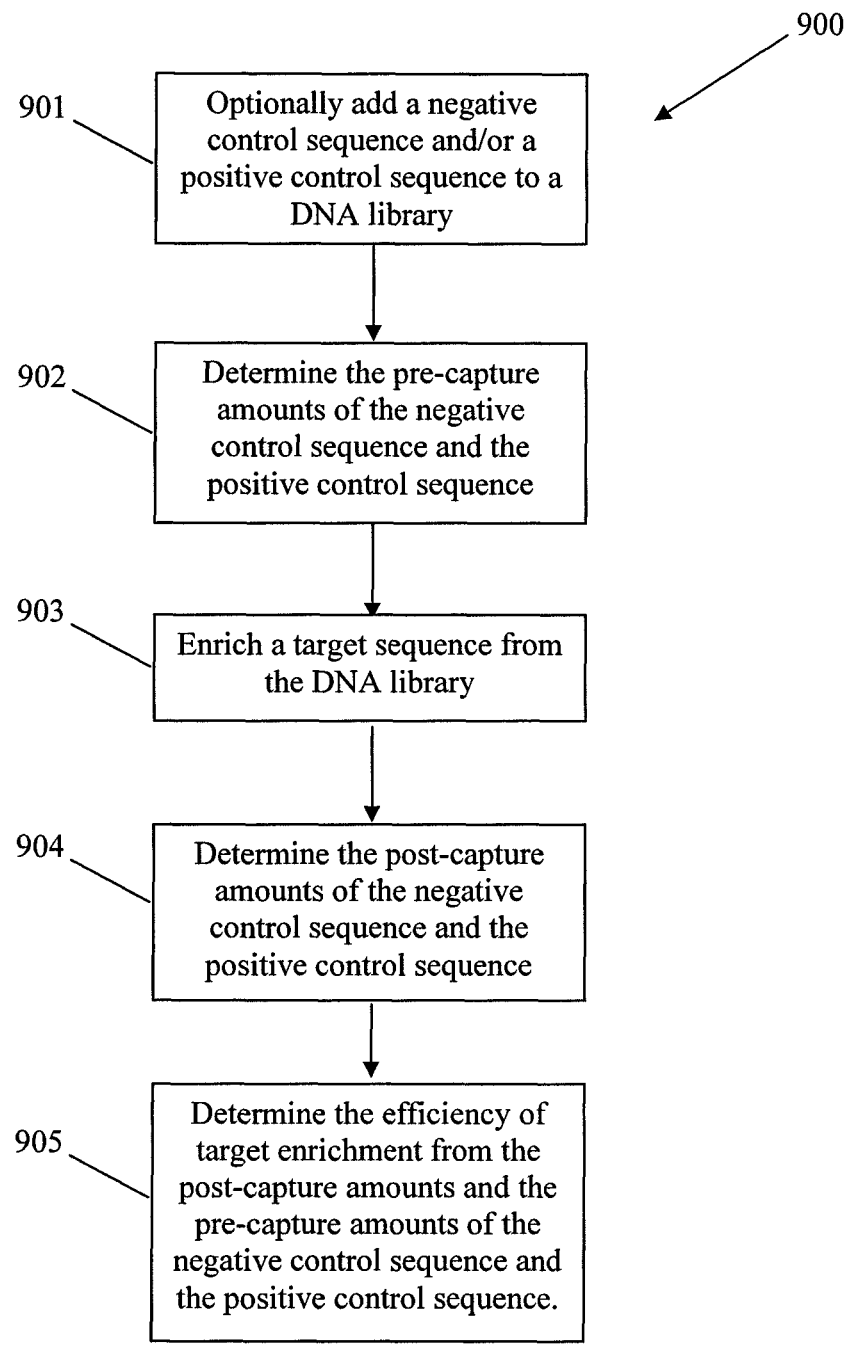
FIG. 9 shows a flowchart illustrating a method in accordance with one embodiment of the invention.

To obtain more accurate estimates of the efficiency of enrichment, one should include one or more positive control sequences, as illustrated in method 900 shown in FIG. 9. As shown in FIG. 9, one may optionally add one or more negative control sequences and/or one or more positive control sequences to a DNA library. (step 901). Again, one may optionally add one or more negative control sequences, or one may use endogenous repeat sequences as negative controls. Similarly, a positive control sequence may be endogenous, i.e., the sequence is originally present in the target library. In some cases, adding an exogenous positive control sequences may be advantageous (e.g., known concentrations). If the amounts of the negative control sequence and the positive control sequence are not known, then one would determine these pre-capture amounts before the enrichment. (step 902). If the amounts of the negative control sequence and the positive control sequence are known or if both sequences are added at the same (or about the same) amount, then one may skip step 902. In this case, the "determining" the amounts of the negative control sequence and the positive control sequence is intended to mean "obtaining" such information. The determination can be performed with qPCR or any other suitable method.

Then, enrichment of the desired target sequence is performed using one of more bait sequences. (step 903). Again, the enrichment can be performed using any commercially available systems and instruments.

After enrichment, the amounts of the negative and positive control sequences are determined (step 904). Finally, the efficiency of the enrichment is determined based on the pre-capture and post-capture amounts of the negative and positive control sequences. (step 905).

To determine the enrichment efficiency based on the pre-capture and post-capture amounts, there are several approaches. First, if the amounts of the negative control and the positive control are added at about the same amount in step 901, then one can simply use the post-capture amounts of the negative and positive sequences to estimate the efficiency. Specifically, the ratio of the post-capture amount of the positive control sequence over the post-capture amount of the negative control sequence would provide a good indication of the enrichment efficiency. One example of this approach is shown in FIG. 7B.

In another approach (useful when the pre-capture amounts of the negative control and the positive control sequences are not (approximately) the same), one can derive a first ratio of the pre-capture amount of the positive control sequence over the pre-capture amount of the negative control sequence, and a second ratio of the post-capture amount of the positive control sequence over the post-capture amount of the negative control sequence. Then, a comparison of the first ratio and the second ratio would provide an estimate of the efficiency of the enrichment.

Library Preparation

A library to be used with embodiments of the invention can be commercially available library or prepared in the laboratory. DNA library preparation may use the commercial kits available from various vendors (e.g., Illumina, Inc.), following the standard protocols for paired-end sequencing. (e.g., "Paired-End Sequencing Sample Preparation Guide," available from Illumina, Inc., San Diego, Calif.). For example, genomic DNA (Coriell, 3 µg) may be fragmented (e.g., by shearing, nebulization, or sonication) to suitable sizes (e.g., 200-500 bp). For example, the shearing may be carried out using a Covaris E210 instrument to median fragment sizes (e.g., 200-250 bp). The ends of these fragments are repaired with a combination of fill-in reactions and exonuclease activity to produce blunt ends. Then, 3' non-template A's are added to the blunt ends. Subsequently, the paired-end adapters are ligated to the DNA fragments. The 5' and 3' end adapters for the Illumina® system are shown below. The library thus prepared may be subjected to size selection on agarose gel (e.g., a 4% Nusieve® 3:1 agarose gel) and purified using QiaQuick® gel extraction. Then, the library may be amplified by a few (e.g., 6-8) cycles of PCR.

Illumina Adapters:

```
P5: AATGATACGGCGACCACCGA      SEQ ID NO: 14

P7: CAAGCAGAAGACGGCATACGA     SEQ ID NO: 15
```

Enrichment of Target Sequences

In accordance with embodiments of the invention, any enrichment system know in the art may be used. Several instruments are available from vendors for the enrichment of target sequences, such as the Illumina® system from Illumina, Inc. and the SureSelect™ systems from Agilent. Embodiments of the invention are not limited by any specific procedures or instrument. Agilent SureSelect™ Target Enrichment System provides specific enrichment of user-defined subsets of a genome. (see, Gnirke et al., Nat. Biotechnol. 27, (2009), pp. 182-189). The method is based on hybridization of genomic DNA libraries to custom biotinylated RNA probes (typically, 120-mer RNA probes) and subsequent immobilization on magnetic beads, followed by wash and elution steps, as illustrated in FIG. 1. This process has been verified in the enrichment of several libraries with different RNA capture probe sets specific to the human X chromosome, all human exons, or regions on chromosome 4. After elution of the captured DNA fragments, the library may be re-amplified for a few cycles (e.g., 12-14 cycles) of PCR with SureSelect™ Illumina®-specific primers (SEQ ID NO: 14 and SEQ ID NO: 15). Amplification enables accurate quantification using the Bioanalyzer High Sensitivity chip or qPCR before sequencing.

Advantages of embodiments of the invention may include one or more of the following. Embodiments of the invention using negative controls are generally applicable. No specific negative controls are needed. Instead, the repeat sequences that are generally found in most genomes may be used as negative controls. In contrast, negative controls that are specifically designed for one library may not be used for a different probe library. Because such specific "negative control" elements are removed from the probe libraries, it is unlikely that the negative controls will be present in the new libraries. Therefore, each time a new negative control would need to be designed.

Embodiments of the invention also can be used to provide ratios of positive controls to negative controls. As shown above, such ratios can be used to estimate enrichments, using only the post-enrichment samples. Because the pre-enrichment samples are not required, one can save time and costs in such enrichment experiments.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining an efficiency of target enrichment from a DNA library, comprising:
   adding a negative control sequence and a positive control sequence to the DNA library, or picking a negative control sequence and a positive control sequence from the DNA library wherein the negative control sequence is selected from the group consisting of SEQ ID NO:1, SEQ ID NO:5, SEQ ID NO: 9, SEQ ID NO: 10, SEQ ID NO: 11, SEQ ID NO: 12 and SEQ ID NO: 13;
   determining, using quantitative PCR (polymerase chain reaction), a pre-capture amount of the negative control sequence and a pre-capture amount of the positive control sequence in the DNA library;
   performing enrichment of a target sequence from the DNA library using at least one bait sequence to produce a post-capture library;
   determining, using quantitative PCR, a post-capture amount of the negative control sequence and a post-capture amount of the positive control sequence in the post-capture library; and
   determining the efficiency of the target enrichment,
   based on a ratio of the post-capture amount of the positive control sequence over the post-capture amount of the negative control sequence, or
   based on comparing (i) a first ratio of the pre-capture amount of the positive control sequence and the pre-capture amount of the negative control sequence, and (ii) a second ratio of the post-capture amount of the positive control sequence and the post-capture amount of the negative control sequence.

2. The method of claim 1, wherein the negative control sequence is AluJo having the sequence of SEQ ID NO: 1.

3. The method of claim 1, wherein the negative control sequence is L1MEe having the sequence of SEQ ID NO: 5.

4. The method of claim 1, wherein the bait sequence comprises an oligomer of ribonucleic acid (RNA).

5. The method of claim 1, wherein the bait sequence is attached to an affinity ligand or a solid support.

6. The method of claim 5, wherein the affinity ligand is biotin.

7. A method for determining an efficiency of target enrichment from a DNA library, comprising:
   adding a negative control sequence to the DNA library, or picking a negative control sequence from the DNA library, wherein the negative control sequence is selected from the group consisting of SEQ ID NO:1, SEQ ID NO:5, SEQ ID NO: 9, SEQ ID NO: 10, SEQ ID NO: 11, SEQ ID NO: 12, and SEQ ID NO: 13;
   determining, using quantitative PCR (polymerase chain reaction), a pre-capture amount of the negative control sequence in the DNA library;
   performing enrichment of a target sequence from the DNA library using at least one bait sequence to produce a post-capture library;
   determining, using quantitative PCR, a post-capture amount of the negative control sequence in the post-capture library;
   determining the efficiency of the target enrichment by comparing the pre-capture amount of the negative control sequence and the post-capture amount of the negative control sequence.

8. The method of claim 7, wherein the negative control sequence is AluJo having the sequence of SEQ ID NO: 1.

9. The method of claim 7, wherein the negative control sequence is L1MEe having the sequence of SEQ ID NO: 5.

10. The method of claim 7, wherein the bait sequence comprises an oligomer of ribonucleic acid (RNA).

11. The method of claim 7, wherein the bait sequence is attached to an affinity ligand or a solid support.

12. The method of claim 11, wherein the affinity ligand is biotin.

* * * * *

UNITED STATES PATENT AND TRADEMARK OFFICE
CERTIFICATE OF CORRECTION

| | | |
|---|---|---|
| PATENT NO. | : 8,663,924 B2 | Page 1 of 1 |
| APPLICATION NO. | : 13/308482 | |
| DATED | : March 4, 2014 | |
| INVENTOR(S) | : Scott Happe et al. | |

It is certified that error appears in the above-identified patent and that said Letters Patent is hereby corrected as shown below:

On the title page, in item (56), under "Other Publications", in column 2, line 1, delete "Tawhey" and insert -- Tewhey --, therefor.

In the Claims

In column 21, line 7, in claim 1, delete "library" and insert -- library, --, therefor.

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 15

<210> SEQ ID NO 1
<211> LENGTH: 311
<212> TYPE: DNA
<213> ORGANISM: Homo Sapiens

<400> SEQUENCE: 1
agctgggcgt ggtggctcac gcctgtaatc ccagaacttt gggaggctga gactggctga      60
tttcttgagc ccaggagttt gagactagcc tggacaacat agtgagaccc catctttaca     120
aaaaaattaa aaaaaattag tggacatggt ggcatgcacc tctagtccca gttactcagg     180
aggctgaggt gggaggatca cctgtgccca ggctgaggct gcagtgagcc atgatcacgc     240
cactgcactc cagcctgcgt gacagagcaa gaccctgtct caaagaaaa gaaaaaaaaa     300 gaagaaagaa a                                                          311

<210> SEQ ID NO 2
<211> LENGTH: 20
<212> TYPE: DNA
<213> ORGANISM: Artificial Sequence
<220> FEATURE:
<223> OTHER INFORMATION: Oilgonucleotide primer

<400> SEQUENCE: 2
gtggcatgca cctctagtcc                                                  20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
tgagacaggg tcttgctctg                                                  20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 4
tactcaggag gctgaggtgg                                                  20

<210> SEQ ID NO 5
```

```
<211> LENGTH: 153
<212> TYPE: DNA
<213> ORGANISM: Homo sapiens

<400> SEQUENCE: 5
atgctattta cgagagaagc atttgcaaca aaatgccaaa gagaaggtga aaatagctgg      60
aaaaaaaatg cgcaaagcaa ataaccaata gaaagaaagc caagttgggc tagcaaaatc     120
agacaaaata accttcgagg tgcaaacaac ttt                                  153

<210> SEQ ID NO 6
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 6
gcgcaaagca ataaccaat                                                   20

<210> SEQ ID NO 7
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 7
tgtttgcacc tcgaaggtta                                                  20

<210> SEQ ID NO 8
<211> LENGTH: 20
<212> TYPE: DNA
<213> ORGANISM: Artificial sequence
<220> FEATURE:
<223> OTHER INFORMATION: Oligonucleotide probe

<400> SEQUENCE: 8
tgggctagca aaatcagaca                                                  20

<210> SEQ ID NO 9
<211> LENGTH: 301
<212> TYPE: DNA
<213> ORGANISM: Homo sapiens

<400> SEQUENCE: 9
ggctggatgc agtggctcgt gcctgtaatc ccaacacttt gggaggctga ggcgggtgga      60
tcacctgagg tcaggagttc gagaccaggc tggccaacat ggcaaaaccc cgcctctact     120
aaaaatacaa aaattagcca ggcatagtgg tgcacgcctg taatcacagc tactcaagag     180
gctgaagcag gagaattgct tgaactcagg aggtggaggt ggcagtgagc caagatcgtg     240
ccactgcact ccagcctcag tgacagagcg agactctgtc tcaaaaaata aataaataaa     300
a                                                                    301

<210> SEQ ID NO 10
<211> LENGTH: 296
<212> TYPE: DNA
<213> ORGANISM: Homo sapiens

<400> SEQUENCE: 10
ggccgggcgc gggggctcgc gcctgtcatc ccagcacttt gggaggccga ggcgggcgga      60
tcacgaggtc aggagatcga gaccatcctg gctaacacgg ggaaacccccg tctccactaa    120
```

| | |
|---|---|
| aaatacaaaa agttagccgg gcgcggtggc gggcgcctgc ggtcccagct gctggggagg | 180 |
| ccgaggcggg agcatggcgg gaaccgggag gcggagcctg cagtgagccg agatggcgcc | 240 |
| accgcactcc agcctgggcg acccagcgag actccgcctc aaaaaaaaaa aaagaa | 296 |

<210> SEQ ID NO 11
<211> LENGTH: 263
<212> TYPE: DNA
<213> ORGANISM: Homo sapiens

<400> SEQUENCE: 11

| | |
|---|---|
| tctctttatt tgcttctgct aattaaaaaa tcagagctaa agatacttaa acactacagt | 60 |
| taaaatgcca tggttgtcta ttggcttaac gaattctctt atgaaatcaa ctctaaaatg | 120 |
| ctatccatca taaatcatga aacgcaattt ttcttattct ctttagagct ttacaattca | 180 |
| tcttaaagac cagtgtttac actctcttct gtaggttgta caataacttt tggcgagaaa | 240 |
| aaataaaagt ctggctttct gac | 263 |

<210> SEQ ID NO 12
<211> LENGTH: 200
<212> TYPE: DNA
<213> ORGANISM: Homo sapiens

<400> SEQUENCE: 12

| | |
|---|---|
| ggaggtggta aatttgactc atgggacaaa tcttttgtaa ataaagtttc actggaaccc | 60 |
| agtcacactc atttgtttct gtattgtctg ttgacagttt ttatgctaca ataagagttg | 120 |
| agtagttatg acagacactc tagggcctgt agagcctata atatttactt ttggccttttt | 180 |
| acggaagaag tttactgacc | 200 |

<210> SEQ ID NO 13
<211> LENGTH: 179
<212> TYPE: DNA
<213> ORGANISM: Homo sapience

<400> SEQUENCE: 13

| | |
|---|---|
| ctcctctgtc ttttcccacc aagtgaggat gcgaagagaa ggtggctgtc tgcaaaccag | 60 |
| gaagagagcc ctcaccggga acccgtccag ctgccacctt gaacttggac ttccaagcct | 120 |
| ccagaactgt gagggataaa tgtatgattt taaagtcgcc cagtgtgtgg tattttgtt | 179 |

<210> SEQ ID NO 14
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 14

| | |
|---|---|
| aatgatacgg cgaccaccga | 20 |

<210> SEQ ID NO 15
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 15

| | |
|---|---|
| caagcagaag acggcatacg a | 21 |